United States Patent [19]

Newbould

[11] Patent Number: 4,587,837
[45] Date of Patent: May 13, 1986

[54] CAPILLARY RHEOMETER HAVING DISPOSABLE CAPILLARY TUBE

[75] Inventor: John Newbould, Fraser, Mich.

[73] Assignee: General Motors Corporation, Detroit, Mich.

[21] Appl. No.: 692,123

[22] Filed: Jan. 17, 1985

[51] Int. Cl.$^4$ ............................................. G01N 11/08
[52] U.S. Cl. ....................................................... 73/56
[58] Field of Search .................. 73/56; 374/45, 54, 55

[56] References Cited

U.S. PATENT DOCUMENTS

| | | | |
|---|---|---|---|
| 2,780,096 | 2/1957 | Noble et al. | 73/56 X |
| 3,270,553 | 9/1966 | Ballman et al. | 73/56 |
| 3,279,240 | 10/1966 | Kowalski | 73/56 X |
| 3,758,776 | 9/1973 | Frohne et al. | 73/56 X |
| 4,313,339 | 2/1982 | Nichols et al. | 73/56 |

FOREIGN PATENT DOCUMENTS 1261692  2/1968  Fed. Rep. of Germany .......... 73/56

Primary Examiner—Stewart J. Levy
Assistant Examiner—Joseph W. Roskos
Attorney, Agent, or Firm—Randy W. Tung

[57] ABSTRACT

An improved capillary rheometer features a barrel surrounded by electrical heating elements which are automatically controlled to maintain constant temperature along the barrel length, a liner for the barrel to hold a sample, a capillary tube retained in a holder that fits in sealing relation with the liner; and a bottom plate which prevents displacement of the capillary tube. The assembly of liner, capillary and holder is easily removed and replaced to provide for quick sample changes and easy cleaning.

2 Claims, 2 Drawing Figures

CAPILLARY RHEOMETER HAVING DISPOSABLE CAPILLARY TUBE

This invention relates to an improved capillary rheometer that is particularly adapted for rapidly measuring the melt viscosity of highly filled polymers at high temperatures.

BACKGROUND

Measuring the rate of extrusion of a molten resin though a capillary of known size under a known applied pressure is a widely accepted method of determining rheological properties of thermoplastic polymers. These test devices are known in the art as capillary rheometers. They comprise a sample cylinder that is generally equipped with a die having a capillary bore drilled in it. There are two common types of capillary rheometers which are distinguished by the means used to force the molten polymer contained in the sample cylinder through the capillary. In one design, the cylinder and die are immersed in a heated oil tank. A stirrer is provided to circulate the oil. The die is fastened to a hole in the bottom of the tank to prevent oil leakage but allow extrusion of a sample through the capillary. Heating the oil in the tank heats the cylinder which heats a polymeric sample retained in it. This type of capillary rheometer uses a pressurized gas to eject the molten sample through the capillary and is much preferred for testing viscous filled resins.

The second type employs a metal piston which fits tightly in the sample cylinder bore and pushes the polymer through the capillary. The whole unit is enclosed in a muffle tube furnace for heating. Such rheometers work well at relatively low shear rates and temperatures for pure, stable polymer resins. However, they do not work well for highly filled polymers tested at relatively high extrusion pressures and temperatures. Measurements may be inaccurate because of friction between the piston and the cylinder wall which is aggravated by the presence of fillers such as fiberglass.

Both types of conventional rheometers have characteristics that make them difficult to use. For example, it is difficult to control oil temperature at test temperatures above about 200° C. It is also extremely difficult to clean the sample cylinders and capillary dies without completely disassembling the apparatus. This leads to long cycle times between measurements. The apparatus must also be disassembled to change the capillary die as its size changes due to abrasion by fillers. The preferred way of cleaning sample cylinders and dies is heating them in a furnace or immersing them in a molten salt bath to burn away the polymer. This also requires complete disassembly of conventional rheometers.

Accordingly, it is an object of this invention to provide an improved capillary rheometer that is more accurate and easily serviceable.

BRIEF SUMMARY

This and other objects are accomplished in accordance with the novel rheometer I have developed. It comprises a cylindrical barrel that is surrounded by a plurality of electrical heating elements that are easily controlled to maintain a constant barrel temperature. The inside bore of the barrel is cylindrical. A barrel liner made of stainless steel or other easily cleaned and corrosion resistant metal is provided which is sized to fit snugly in the barrel bore. A cylindrical capillary tube having a capillary bore of the desired size for a particular test is provided. This tube is press-fit in a cylindrical capillary holder whose outside diameter fits snugly in the barrel liner. A bottom plate is secured beneath the barrel to prevent movement of the liner, holder and capillary when pressure is applied to a sample. A top plate with a gas inlet is sealably mounted to the top of the barrel.

The barrel is preferably mounted on a stand so that a sample can be introduced into the top of the barrel liner and be ejected below the barrel into a weighing dish or receptacle. A polymer sample to be tested is placed in the barrel liner. A source of a pressurized gas such as nitrogen is provided above the sample. The gas is delivered through a pressure regulator to a tube which is attached by a leak-proof seal to the top plate. To measure the rheological properties of a sample, the barrel is heated to the desired temperature by the band heaters. Gas is let into the barrel above the molten sample at a controlled pressure. The rate of extrusion of the sample through the capillary is measured. Such properties as shear rate and melt viscosity can be calculated from the extrusion data.

An advantage of the subject rheometer is that to run another sample, the operator need only remove the top or bottom plates and insert a clean assembly of liner, capillary and capillary holder to run a different sample. The dirty assembly can be easily cleaned in a furnace or salt bath. The subject apparatus not only permits a rapid test cycle time but the complete removal of any decomposed resin or gel which can clog the capillary in subsequent runs and cause faulty measurements. Furthermore, easy removal and replacement of the capillary tube eliminates cumulative errors which can occur by abrasion and widening of the capillaries by mineral fillers.

DETAILED DESCRIPTION

The invention will be better understood in view of the Figures and detailed description which follow.

Figures 1, 2:
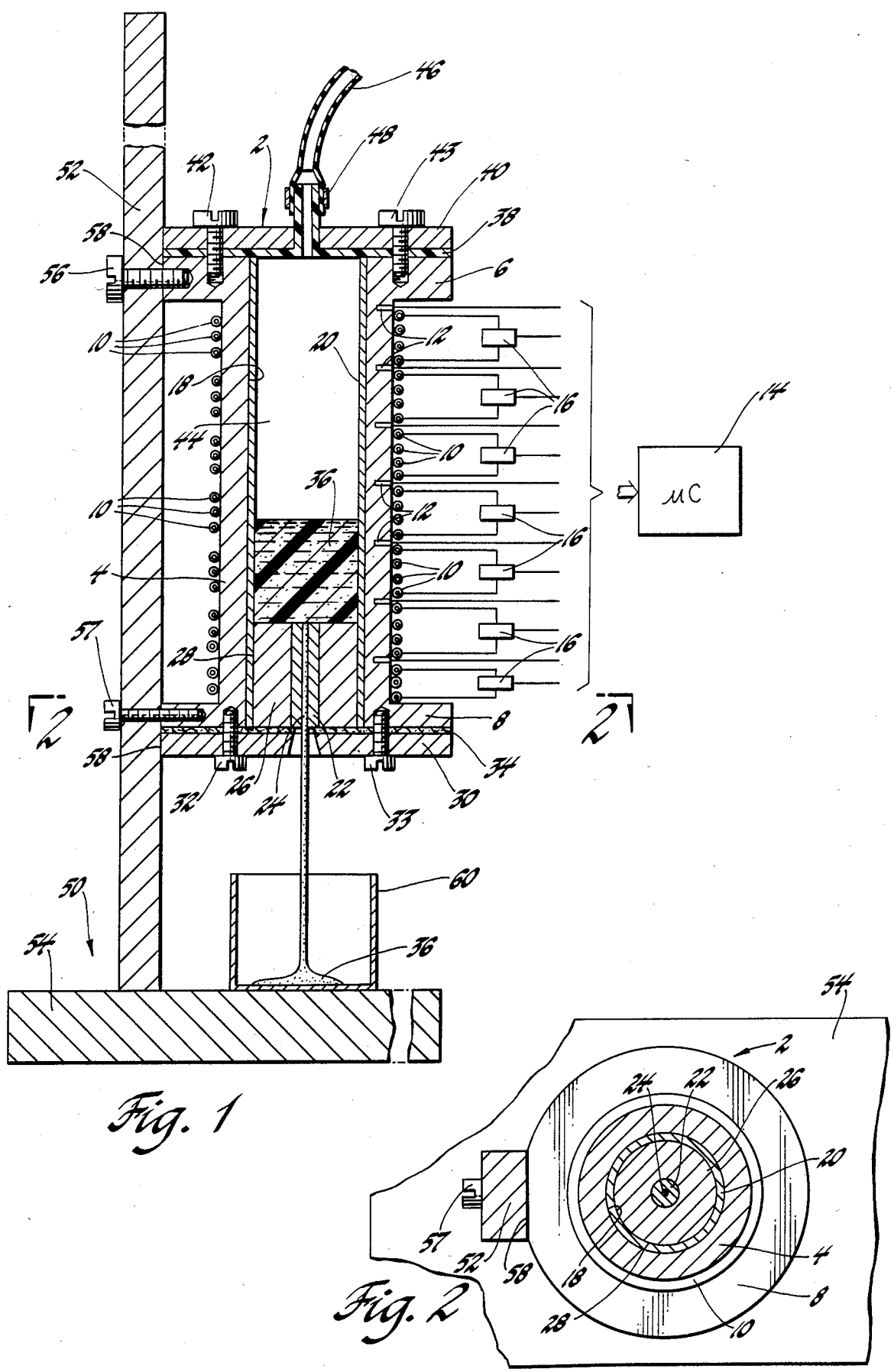
FIG. 1 is a schematic sectional view of a capillary rheometer in accordance with this invention which is mounted on a stand.
FIG. 2 is a plan view of the barrel, liner, capillary holder and capillary taken along 2—2 of FIG. 1.

Referring to FIGS. 1 and 2, the rheometer 2 comprises a cylindrical barrel 4 that has a top flange 6 and a bottom flange 8. Barrel 4 is surrounded by a plurality of electrical band heaters 10. Thermocouples 12 are located in holes drilled into barrel 4. Output from thermocouples 12 is fed to a microcomputer 14 (or solid state temperature controller). Based on the thermocouple ouput, microcomputer 14 controls switches 16 to turn band heaters 10 on and off to maintain the desired temperature along the barrel. Switches 16 may be solid state or electromechanical. It is highly desirable to maintain a constant temperature along the entire length of barrel 4.

Inside bore 18 of barrel 4 is preferably right circular cylindrical. A barrel liner 20 made of stainless steel or other easily cleaned and corrosion resistant metal is provided which is sized to fit snugly in barrel bore 18. A cylindrical capillary tube 22 having a capillary of the desired size for a particular test is provided. Capillary tube 22 is preferably press-fit in cylindrical capillary holder 26 whose outside surface 28 fits snugly in barrel liner 20.

Bottom plate 30 is secured beneath lower barrel flange 8 with bolts 32 and 33 and leak proof gasket 34 is inserted between them. Gasket 34 and bottom plate 30 have holes in the center sized to allow resin 36 extruded through capillary 24 to fall freely but to prevent dislocation of capillary tube 22.

An integral gasket 38 and gas inlet port 48 which is preferably made of a heat resistant material such as polytetrafluoroethylene is positioned over top flange 6. Gasket 38 and top plate 40 are secured to barrel flange 6 by bolts 42 and 43. A pressurized gas such as nitrogen is introduced into liner bore 44 by means of an inlet tube 46 held in place by clamp 48.

Rheometer 2 is shown attached to a portable stand comprising an upright standard 52 and a base 54. The rheometer is attached to standard 52 by bolts 56 and 57. As shown in FIG. 2, the rheometer flanges, gaskets and plates may be flattened at edge 58 to butt tightly against a square standard 52. A cup 60 may be provided beneath capillary 24 to catch extruded resin 36.

Rheometric measurements are made by inserting a capillary tube 22 having a capillary 24 of the desired size in tube holder 26. The tube holder is inserted in liner 20, a resin sample 36 is introduced, and the assembly is inserted in bore 18 of barrel 4. Capillary tube 22 and holder 26 may be replaced by a single die having a capillary running through it.

Top plate 40 and insert 38 are positioned and sealably secured above barrel flange 6. Heater bands 10 are turned on until the desired temperature is reached along the barrel length. At this time, a gas that is inert to the polymer sample is introduced through tube 46 at a known pressure. This forces resin 36 to flow through capillary 24 into cup 60. The pressure exerted by the gas is a measure of the shearing stress and the amount of resin extruded per unit time is a measure of shear rate. These values can be recorded manually or automatically by means well known in the art. Other values such as melt viscosity can be calculated using this data.

After a resin sample 36 has been run, all that need be done to run another sample is to remove either or both the top plate and insert or bottom plate and gasket. The liner/tube holder/capillary tube assembly is then pulled or pushed out of barrel 4. A clean assembly containing a different sample is inserted in the barrel, the barrel is sealed and the new sample is run. Any resin remaining on the first sample assembly can easily be burnt off in an oven or a molten salt bath. The subject apparatus is particularly well adapted to testing polymers containing abrasive mineral fillers such as fiberglass, mica, metal flake, asbestos or talc. All such fillers tend to abrade and increase the size of the capillary. It is therefore very advantageous to be able to quickly and cleanly change capillary tubes when running several samples.

While my invention has been described in terms of specific embodiments thereof, other forms may be readily adapted by one skilled in the art. Accordingly, my invention is to be limited only by the following claims.

The embodiments of the invention in which an exclusive property or privilege is claimed are defined as follows:

1. In a device for measuring the rheometric properties of molten polymeric materials by expressing them through a capillary, the improvement comprising a barrel surrounded by a plurality of electrical heating elements which are automatically controlled to maintain a constant temperature along the length of the barrel; a liner which fits securely in the bore of the barrel for retaining a polymeric sample; a disposable capillary tube having a capillary through which the polymeric sample is extruded by application of positive gas pressure above the sample; a capillary tube holder which fits in sealing relation between the said liner and the capillary tube; and a separate bottom plate which prevents the capillary tube from moving when said polymeric material sample is extruded therethrough, wherein said device, the said liner, capillary tube, and tube holder may be readily removed and replaced by like components to facilitate quick sample changes and easy cleaning thereof.

2. In a rheometer for measuring the rheometric properties of molten polymeric materials by expressing them through a capillary, the improvement comprising a barrel surrounded by a plurality of electrical heating elements which are automatically controlled to maintain a constant temperature along the length of the barrel; a liner which fits securely in the bore of the barrel for retaining a polymeric sample; a die which fits in sealing relation within the liner and has a press-fitted disposable capillary tube through which the polymeric sample is extruded by application of positive gas pressure above the sample; and a bottom plate which prevents the die from moving when said polymeric material sample is extruded therethrough, wherein said rheometer, the said liner, said die and disposable capillary tube may be readily removed and replaced by like components to facilitate quick sample changes and easy cleaning thereof.

* * * * *